United States Patent [19]

Feyen et al.

[11] 4,416,834
[45] Nov. 22, 1983

[54] PROCESS FOR THE PREPARATION OF THIOPHOSPHORIC ACID ESTERS

[75] Inventors: Peter Feyen, Mettmann; Friedrich Schmidt, Wuppertal, both of Fed. Rep. of Germany

[73] Assignee: Bayer Aktiengesellschaft, Leverkusen, Fed. Rep. of Germany

[21] Appl. No.: 190,288

[22] Filed: Sep. 24, 1980

[30] Foreign Application Priority Data

Oct. 13, 1979 [DE] Fed. Rep. of Germany ....... 2941587

[51] Int. Cl.[3] ............................................... C07F 9/165
[52] U.S. Cl. ...................................... 260/979; 260/948
[58] Field of Search ......................................... 260/979

[56] References Cited

U.S. PATENT DOCUMENTS 2,759,010 8/1956 Lorenz et al. ........................ 260/979
2,873,228 2/1959 Willard et al. ....................... 260/979
3,829,535 8/1974 Mueller et al. ...................... 260/979

Primary Examiner—Anton H. Sutto
Attorney, Agent, or Firm—Sprung, Horn, Kramer & Woods

[57] ABSTRACT

A process for the preparation of a compound of the formula

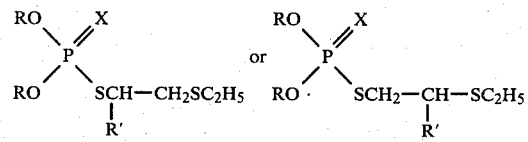

in which

R is alkyl,
X is oxygen or sulphur and
R' is hydrogen or alkyl, comprising reacting a thiophosphate of the formula

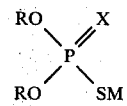

in which M is a cation other than $NH_4^\oplus$, with an ethylmercapto compound of the formula

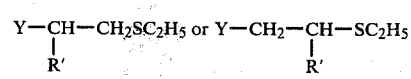

in which Y is a fugitive group, in a polar reaction medium at a temperature between about 30° and 80° C. and at a pH between about 2 and 9. Advantageously X is oxygen and the thiophosphate is produced by reaction of a dialkyl phosphite of the formula

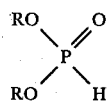

with sulphur in the presence of an organic base in an organic solvent and subsequent extraction with aqueous MOH solution. Also Y is advantageously chlorine and the ethylmercapto compound is prepared by heating the corresponding alcohol to about 40°–100° C. and passing hydrogen chloride gas into the pre-warmed alcohol, the reaction solution being used directly without working up.

6 Claims, No Drawings

PROCESS FOR THE PREPARATION OF THIOPHOSPHORIC ACID ESTERS

The invention relates to an unobvious process for the preparation of certain known thiophosphoric acid esters which are used as insecticides and acaricides with a systemic action or are employed as starting substances for the preparation of chemical compounds which exhibit a similar action.

The compounds can be described by the following general formula:

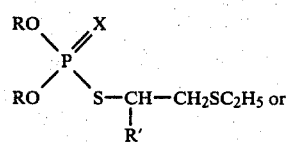

in which
R represents alkyl,
R' represents H or alkyl and
X represents S or O, for example: Ia, in which R=CH$_3$, R'=H and X=O; Ib, in which R=CH$_3$, R'=H and X=S; Ic, in which R=C$_2$H$_5$, R'=H and X=S; and Id, in which R=CH$_3$, R'=CH$_3$ and X=O.

The route which was probably the best hitherto used for the preparation of these compounds may be described using the following example:

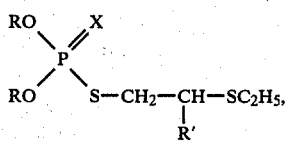

about 40% strength in water
Yield: 95%
Toluene employed again

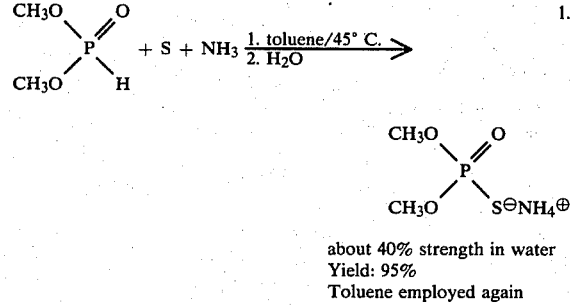

Yield: about 90–95%

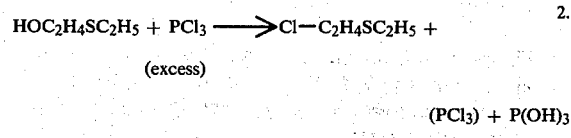

from Stage 1          from Stage 2
(excess)

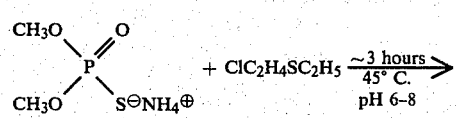

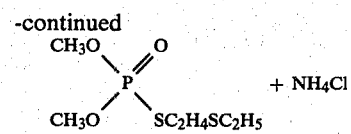

Yield: about 83%, relative to the alcohol in Stage 2.

The individual stages are described in the following references: 1st Stage: Houben-Weyl, Volume 12/II, 602 and 603, and German Pat. No. 835,145; 2nd Stage: Houben-Weyl, Volume 5/3; 3rd Stage: German Pat. No. 836,349, German Pat. No. 830,509, U.S. Pat. No. 2,571,989, G. Schrader: Die Entwicklung neuer insektizider Phosphorsäureester (The Development of New Insecticidal Phosphoric Acid Esters), page 408 and R. Wegler, Chemie der Pflanzenschutz und Schädlingsbekämpfungsmittel (Chemistry of Plant Protection and of Agents for Combating Pests), Volume 1, page 331 et seq., Springer Verlag 1970.

This process has the following disadvantages:
1. The use of ammonia (liquid or gaseous) is a safety risk.
2. The removal of the resulting ammonium chloride from the effluent, which is necessary for ecological reasons, is expensive.
3. The phosphorous acid obtained in Stage 2 (together with excess PCl$_3$) on the one hand gives rise to side reactions in Stage 3 and on the other hand finally enters the effluent, from which it must be removed, also at great cost.
4. The material costs are high as a result of using phosphorus trichloride and dimethyl thiophosphate in excess, and significant formation of by-products occurs.

The present invention now provides a process for the preparation of a compound of the formula (I), in which R represents alkyl, X represents oxygen or sulphur and R' represents hydrogen or alkyl, in which a phosphate of the general formula

in which
R denotes alkyl,
X denotes oxygen or sulphur and
M denotes a cation (with the exception of NH$_4^+$), is reacted with a compound of the general formula

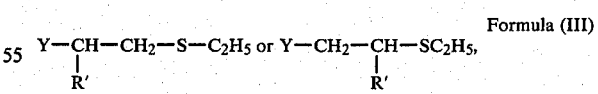

in which
R' is alkyl or hydrogen and
Y is a fugitive group.

The reaction takes place in a polar medium. The pH value is between about 2 and 9. The reaction temperature should be about 30°–80° C., so that the reaction times are between about 30 minutes and 4 hours.

The concentration, in the reaction medium, of the salt of the formula (II) employed is preferably between 20 and 40% at the start of the reaction. The reaction solution must be thoroughly mixed.

The salt of the formula (II) is employed in stoichiometric amounts or in about 1-2% excess, relative to the compound of the formula (III).

The starting substances of the formula (II) and (III) can be prepared by known processes (see, for example, R. Wegler, Chemie der Pflanzenschutz- und Schädlinkgsbekämpfungsmittel (Chemistry of Plant Protection Agents and Agents for Combating Pests), Volume 1, page 281 et seq., or Houben-Weyl, Volume 5/3).

In a particular embodiment of the process of the present invention, a compound of the formula (II) in which R is alkyl, X is O and M is a cation is prepared in the following way:

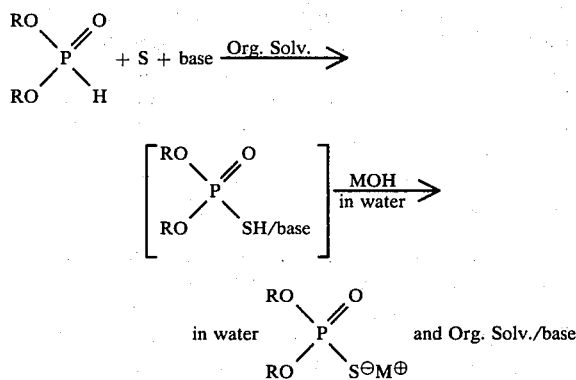

(Org.Solv.=organic solvent; M=metal radical, in particular an alkali metal or alkaline earth metal, preferably Na or K).

The organic phase (solvent+base) is employed again in a subsequent batch.

The reaction temperature is about 40°-80° C.

The invention also includes a preparative process for a compound of the formula (III) in which Y denotes chloride and R' denotes H or alkyl (especially methyl), characterized in that the corresponding alcohol (that is to say Y = OH), HOC$_2$H$_4$SC$_2$H$_5$ or HO—CH—CH$_2$SC$_2$H$_5$ or
$\quad\quad\quad\quad\quad\quad\quad\quad\quad\quad\quad\quad\;\;$ |
$\quad\quad\quad\quad\quad\quad\quad\quad\quad\quad\quad\quad\;\;$ R'

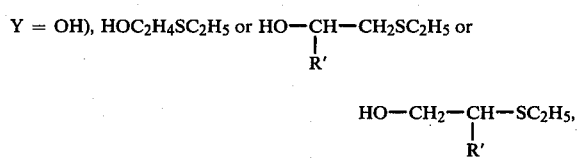

is reacted with hydrogen chloride gas and the reaction solution is employed directly (without working up) in the final stage.

The higher the temperature of the alcohol initially introduced, the more rapidly the gas can be passed in.

The reaction temperature is about 40°-100° C., for example 65°-85° C.

Not only are the compounds of the formula (I) prepared in a higher yield by the process according to the invention compared with conventional processes, but at the same time an effluent which is free from NH$_4$Cl and free from P(OH)$_3$ is obtained. Furthermore, the chemical oxygen requirement is lower and the biological degradability is greater than in the case of effluents obtained in the earlier preparative processes.

Finally, it is now possible to carry out, for example, oxidative treatment of the effluent, which can present problems in the case of effluents containing ammonium chloride (in particular, the formation of explosive and/or bacteriotoxic oxidation products of NH$_4$Cl).

If, for example, dimethyl phosphite and ethylthioethanol are used as starting substances, the desired compound can be obtained according to the following equation:

1:1:1 Mol

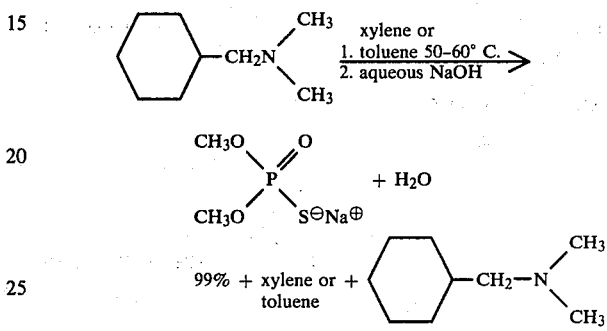

After azeotropic drying, the organic phase is employed again.

HO—C$_2$H$_4$SC$_2$H$_5$ + HCl (gas) $\xrightarrow{65-85°\,C.}$     2.

1:1.15 mols $\quad\quad\quad\quad\quad\quad\quad$ Cl—C$_2$H$_4$SC$_2$H$_5$ + H$_2$O + HCl from $\quad\quad\quad\quad\quad\quad\quad\quad$ to 99% $\quad\quad\quad\quad$ (excess)

Reaction solutions 1 + 2 $\quad\quad\quad\quad\quad\quad\quad\quad\quad$ 3.

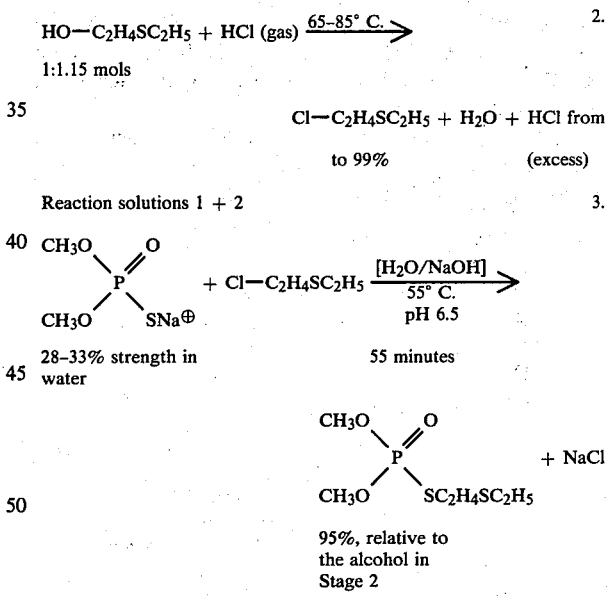

95%, relative to
the alcohol in
Stage 2

The preferred starting compounds of the formula (II) are those in which R represents methyl or ethyl, M represents a sodium or potassium ion and X represents sulphur or oxygen.

In a preferred embodiment of the preparative process of the present invention, the compound of the formula

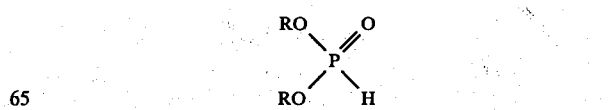

in which
R is CH$_3$ or C$_2$H$_5$, is reacted with sulphur and a water free base in an organic solvent and the salt of the formula (II) is obtained from the reaction solution by extraction with potassium hydroxide or sodium hydroxide in water.

The salt of the formula (II) is then in the aqueous phase and the base is in the organic solvent. After phase separation, rinsing with water and drying, the organic phase can be employed again.

Bases which are employed are those substances which are soluble in organic solvents, preferably amines, such as dimethylbenzylamide, dimethylaniline or triethylamine, and very particularly preferably dimethylbenzylamine.

Preferred "organic solvents" are inexpensive organic substances, such as xylene or toluene, preferably toluene.

In a particular variation of this embodiment, the preparation is carried out continuously, for example in a three-stage cascade of kettles. The reaction temperature is generally 40°-80° C., preferably 45°-65° C.

The second starting compound of the formula (III) in which Y represents a fugitive group, preferably chloride or bromide, and R' represents H or alkyl, preferably methyl, can most simply be obtained by reacting the corresponding alcohols with a halogenating agent (see Houben-Weyl, Volume 5/3).

In a particular preparation variant, which also is according to the present invention, hydrogen chloride gas is used as the halogenating agent.

This gas is passed into the pre-warmed alcohol at 40°-100° C. and, when the introduction has ended, the mixture is subsequently stirred for a further period at 70°-95° C. The complete reaction solution, which consists of an organic upper phase and an aqueous lower phase (phase ratio: 3-5 to 1), is then employed in the final stage without working up.

The hydrogen chloride is generally employed in a slight excess relative to the alcohol, preferably 1.05-1.3 molar equivalents.

In the reaction to give the end product of the formula (I), the salt of the formula (II) obtained in Stage 1 is reacted with the compound of the formula (III) obtained in Stage 2.

Preferably, in formula (I), R represents methyl or ethyl, X represents oxygen or sulphur and R' represents hydrogen or methyl.

Possible diluents are polar substances, preferably water.

The concentration, in the reaction mixture, of the salt of the formula (II) employed should be between about 20 and 40% at the start of the reaction, which is most simply achieved by initially introducing the thiophosphate or dithiophosphate of the formula (II) in the diluent in a concentration of about 25-38% strength, and then adding the compound of the formula (III).

The reaction temperature is between 30° and 80° C., and is preferably about 45° to 65° C.

The pressure in general corresponds to atmospheric pressure. The reaction mixture must be thoroughly stirred.

The pH value should be between about 2 and 9, and is preferably between about 5.0 and 7.5.

In carrying out the process according to the invention, 1.0 to 1.02 mols of the compound of the formula (II) are preferably employed per mol of the compound of the formula (III).

The reaction solution is heterogeneous, that is to say a polar phase is mixed with an organic phase. In certain cases, it is favorable to dilute the compounds of the formula (III) with an organic solvent, for example xylene or toluene, in order thereby to increase the amount of organic phase in the reaction medium.

The reaction product is then obtained predominantly in the organic phase, so that subsequent reactions in the polar phase are diminished.

In general, the reaction product forms the organic phase at the end of the reaction. This phase is separated off and the residues are obtained from the polar phase by extraction with a non-polar substance.

The compounds (I) are well tolerated by plants, have a favorable level of toxicity to warm-blooded animals, and can be used for combating arthropod pests, especially insects or acarids which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and Thrips tabaci;

from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *La-*

*phygma exigua, Mamestra brassicae, Panolis flammea, Prodenia litura,* Spodoptera spp., Trichoplusia ni, *Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example Scorpio maurus and *Latrodectus mactans;* from the order of the Acarina, for example Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

The process according to the present invention is illustrated by the following preparative examples:

EXAMPLE 1

Preparation of sodium dimethyl thiophosphate solution

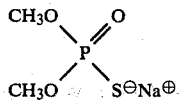

Materials employed: 137.7 g (1.02 mol) of dimethylbenzylamine, 320 ml of xylene, 33.6 g (1.05 mol) of sulphur, 110 g (1.0 mol) of dimethyl phosphite and 168 g (1.05 mol) of sodium hydroxide solution.

The xylene, dimethylbenzylamine and sulphur were initially introduced into a stirred apparatus. A vacuum of about 70 mbars was applied. Dimethyl phosphite was initially added until the temperature reached about 45° C. (about 10 g). Dimethyl phosphite was then further added dropwise as rapidly as possible under 70 mbars and at 45°–50° C., with evaporative cooling. When the addition had ended, the mixture was subsequently stirred for about 30 minutes, after which the solution was cooled to about 30°–40° C. If sulphur was still present, this was filtered off. The sodium hydroxide solution was then added rapidly and the mixture was stirred for some minutes.

The phases were then separated, the aqueous phase was washed once with 80 ml of xylene and the xylene was added to the organic phase, which could be employed again after washing with water and azeotropic drying.

The aqueous phase was weighed and its content was determined, for example, by high pressure liquid chromatography.
Yield: 98%–100% of theory.

The content of the salt in the water was between 50 and 55%, and the pH should be between 11.5 and 13.5.
Alternatives:
1. Instead of dimethylbenzylamine, it is also possible to employ other amines, for example triethylamine, dimethylamine or aniline.
2. The reaction temperature chosen can also be greater than 45°–50° C., whereupon, for example, a continuous preparation in a two- or three-stage cascade of kettles, for example at 60° C., becomes of interest.
3. Xylene can be prepared by other solvents, for example toluene, and the sodium hydroxide solution can be replaced, for example, by potassium hydroxide solution.

EXAMPLE 2

Preparation of 2-(ethylmercapto)-ethyl chloride

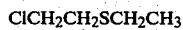
ClCH2CH2SCH2CH3

Materials employed: 106 g (1 mol) of 2-(ethylmercapto)-ethanol and 42 g (1.15 mol) of hydrogen chloride gas.

The 2-(ethylmercapto)-ethanol was initially introduced into a stirred apparatus at 85° C. and HCl gas was then passed in at the same temperature in the course of 45 minutes.

The mixture was then subsequently stirred for a further 25 minutes at 85° C. and the solution was cooled to room temperature. About 121 g of an upper phase (99% of 2-(ethylmercapto)-ethyl chloride) and about 27 g of a lower phase, which also contained about 3 g of product, were obtained, in addition to water of reaction (18 g) and the excess hydrochloric acid (5.5 g).

The yield (product in the upper phase+product in the lower phase) was 99% of theory.

The reaction solution was further employed directly (see Example 3). Alternatives: the reaction temperature can be varied within wide limits (45°–100° C.) and the metering of the HCl gas can be accordingly shortened or extended.

EXAMPLE 2a

This example was carried out as Example 2, but HCl gas was passed in at 45° C. in the course of 3 hours and the mixture was then stirred for a further 45 minutes at 70° C.

EXAMPLE 3

Preparation of O,O-dimethyl S-(ethylmercaptoethyl) thiophosphate

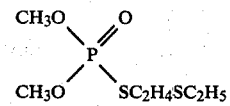

Materials employed: (1) reaction solution from Example 2 and (2) 162.4 g (0.99 mol) of sodium dimethylthiophosphate as a 33% strength solution in water (reaction solution from Example 1 diluted with water).

The sodium salt solution was initially introduced into a stirred apparatus and the lower phase of the reaction solution from Example 2 (predominantly aqueous hydrochloric acid) was added such that the pH value did not exceed 6 (addition of 30% strength sodium hydroxide solution). The upper phase was then metered in at pH 6.5. The mixture was warmed to 55° C. for 50 minutes, the pH value being kept at 6.5. The phases were then separated and the aqueous phase was subsequently extracted 3 times with 10% by volume of xylene each time. The organic phases were combined, the water was again separated off and the organic phase was concentrated in vacuo. Yield: 93% of theory. Content according to gas chromatography: 96–99%.

EXAMPLE 4

Preparation of 2-(ethylmercapto)-isopropyl chloride

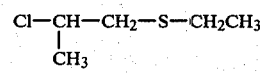

Materials employed: 120 g (1 mol) of 2-ethylmercapto-1-methyl-ethanol and 42 g (1.15 mol) of hydrogen chloride gas The alcohol was initially introduced into a stirred apparatus at 70°–75° C., the HCl gas was passed in at the same temperature in the course of 40 minutes and the mixture was then subsequently stirred at 80°–85° C. for 30 minutes.

The two-phase reaction solution was further processed as such (see Example 5).

Yield of 2-(ethylmercapto)-isopropyl chloride (upper phase+lower phase): 99% of theory.

Weight of the upper phase: 138 g

Weight of the lower phase: 24 g

EXAMPLE 5

Preparation of O,O-dimethyl S-[(2-ethylmercapto)-1-methyl-ethyl]-thiophosphate

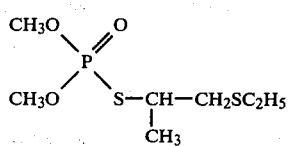

Materials employed: (1) reaction solution from Example 4 and (2) 167 g (1.02 mol) of sodium dimethyl thiophosphate as a 30% strength solution in water, the reaction solution from Example 1 diluted with water.

The procedure was as in Example 3, with the differences that the reaction time was 1.5 hours and the reaction temperature was 65° C.

Yield: 95% of theory; content: about 98%, according to gas chromatography.

It will be appreciated that the instant specification and examples are set forth by way of illustration and not limitation, and that various modifications and changes may be made without departing from the spirit and scope of the present invention.

What is claimed is:

1. A process for the preparation of a compound of the formula

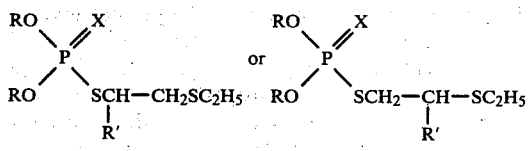

in which
R is alkyl,
X is oxygen or sulphur and
R' is hydrogen or alkyl,
comprising reacting an ethylmercapto compound of the formula

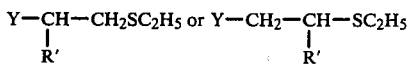

in which
Y is chlorine or bromine, with about 1 to 1.02 times the molar amount of a thiophosphate of the formula

in which
M is a cation other than $NH_4^{\oplus}$, in an aqueous heterogeneous reaction medium at a temperature between about 45° and 65° C. and at a pH between about 5 and 7.5.

2. A process according to claim 1, wherein the thiophosphate is present in the reaction medium in a concentration of about 20–40% by weight at the start of the reaction.

3. A process according to claim 1, wherein the reaction is effected at about 45° to 65° C.

4. A process according to claim 1, wherein R is methyl or ethyl, and R' is hydrogen or methyl.

5. A process according to claim 1, wherein M is an alkali metal ion or an alkaline earth metal ion.

6. A process according to claim 4 wherein X is oxygen M is potassium or sodium, and Y is chlorine.

* * * * *